United States Patent
Tsai et al.

(10) Patent No.: US 10,588,573 B2
(45) Date of Patent: Mar. 17, 2020

(54) DATUM WARNING METHOD, DATUM REBUILDING METHOD, BIO-SENSOR MODULE AND WEARABLE ELECTRONIC DEVICE WITH A DATUM WARNING FUNCTION AND A DATUM REBUILDING FUNCTION

(71) Applicant: PixArt Imaging Inc., Hsin-Chu (TW)

(72) Inventors: Chen-Han Tsai, Hsin-Chu (TW); Hsiu-Ling Yeh, Hsin-Chu (TW); Yung-Chang Lin, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 0 days.

(21) Appl. No.: 15/995,090

(22) Filed: May 31, 2018

(65) Prior Publication Data
US 2019/0365331 A1    Dec. 5, 2019

(51) Int. Cl.
| | |
|---|---|
| *G08B 1/08* | (2006.01) |
| *A61B 5/00* | (2006.01) |
| *G08B 21/24* | (2006.01) |
| *G08B 21/18* | (2006.01) |
| *A61B 5/145* | (2006.01) |
| *A61B 5/021* | (2006.01) |

(52) U.S. Cl.
CPC ............ *A61B 5/7207* (2013.01); *A61B 5/681* (2013.01); *A61B 5/7282* (2013.01); *A61B 5/7405* (2013.01); *A61B 5/746* (2013.01); *A61B 5/7425* (2013.01); *G08B 21/182* (2013.01); *G08B 21/24* (2013.01); *A61B 5/021* (2013.01); *A61B 5/14532* (2013.01)

(58) Field of Classification Search
None
See application file for complete search history.

(56) References Cited

U.S. PATENT DOCUMENTS

| | | | | |
|---|---|---|---|---|
| 2015/0279022 | A1* | 10/2015 | Shuster | ................ H04N 13/332 345/427 |
| 2018/0228462 | A1* | 8/2018 | Maghsoudnia | .......... A61B 8/08 |
| 2018/0260448 | A1* | 9/2018 | Osotio | ................ G06F 16/9024 |

\* cited by examiner

*Primary Examiner* — Adolf Dsouza
(74) *Attorney, Agent, or Firm* — Winston Hsu

(57) ABSTRACT

A datum warning method and a datum rebuilding method are applied to a bio-sensor module equipped in a wearable electronic device. The wearable electronic device includes a warning interface and a bio-sensor module coupled with the warning interface. The bio-sensor module includes a sensor and a processor electrically connected with the sensor. The sensor is adapted to continuously receive a plurality of physical signal. The processor is adapted to identify if one specific physical signal meets a predefined condition, and output a warning signal to show a reminder via the warning interface when the specific physical signal is identified. Further, the processor is adapted to display each of the physical signals via the warning interface, and replace at least one of the physical signals and then store the replaced physical signal with non-replaced physical signals for rebuilding a statistic curve.

4 Claims, 6 Drawing Sheets

DATUM WARNING METHOD, DATUM REBUILDING METHOD, BIO-SENSOR MODULE AND WEARABLE ELECTRONIC DEVICE WITH A DATUM WARNING FUNCTION AND A DATUM REBUILDING FUNCTION

BACKGROUND OF THE INVENTION

1. Field of the Invention

The present invention relates to a wearable electronic device having a bio-senor module, and more particularly, to a bio-sensor module and a related wearable electronic device with a datum warning function and a datum rebuilding function.

2. Description of the Prior Art

A wearable electronic device has a bio-sensor module and a belt assembled with each other. The belt is utilized to stabilize the bio-sensor module on a limb of the user, such as a wrist, and the bio-sensor module is utilized to sense biometric features of the user who wears the wearable electronic device. A conventional algorithm of the wearable electronic device can analyze sensing results of the bio-sensor module in real time to compute and show photoplethysmography (PPG) data on a display of the wearable electronic device for visual observation. When the user exercises, the belt may be shifted around the wrist due to gravity and the bio-sensor module may be spaced from the wrist occasionally. The bio-sensor module cannot acquire correct sensing results since the bio-sensor module and the wrist are separated, so that the user may see unreliable photoplethysmography data on the display of the wearable electronic device within some specific periods of time. Thus, design of an advanced algorithm capable of filtering and amending unreliable noise during bio-detection is an important issue in the related industry.

SUMMARY OF THE INVENTION

The present invention provides a bio-sensor module and a related wearable electronic device with a datum warning function and a datum rebuilding function for solving above drawbacks.

According to the claimed invention, a datum warning method is applied to a bio-sensor module equipped in a wearable electronic device. The datum warning method includes continuously receiving a plurality of physical signals, identifying if one specific physical signal meets a predefined condition, and outputting a warning signal to show a reminder when the specific physical signal is identified.

According to the claimed invention, a datum rebuilding method is applied to a bio-sensor module equipped in a wearable electronic device. The datum rebuilding method includes continuously receiving a plurality of physical signals acquired within a period of time, displaying each of the physical signals, and replacing at least one of the physical signals and then storing the replaced physical signal with non-replaced physical signals before outputting to an external device.

According to the claimed invention, a wearable electronic device with a datum warning function includes a warning interface and a bio-sensor module coupled with the warning interface. The bio-sensor module includes a sensor and a processor electrically connected with the sensor. The sensor is adapted to continuously receive a plurality of physical signal. The processor is adapted to identify if one specific physical signal meets a predefined condition, and output a warning signal to show a reminder via the warning interface when the specific physical signal is identified.

According to the claimed invention, a bio-sensor module with a datum rebuilding function includes a sensor and a processor electrically connected with the sensor. The sensor is adapted to continuously receive a plurality of physical signals acquired within a period of time. The processor is adapted to replace at least one of the physical signals and then storing the replaced physical signal with non-replaced physical signals before outputting to an external device, wherein the replaced physical signal and the non-replaced physical signals are utilized to rebuild a statistic curve.

According to the claimed invention, a wearable electronic device with a datum rebuilding function and a datum warning function includes a warning interface and a sensor module coupled with the warning interface. The sensor module includes a sensor and a processor electrically connected with the sensor. The sensor is adapted to continuously receive a plurality of physical signals acquired within a period of time. The processor is adapted to display each of the physical signals via the warning interface, and replace at least one of the physical signals and then store the replaced physical signal with non-replaced physical signals for rebuilding a statistic curve.

The bio-sensor module can receive the physical signals when the wearable electronic device is actuated and worn by the user. As the bio-sensor module leaves the user's skin, the specific physical signal is identified and the wearable electronic device can output the reminder via the warning interface immediately, but the real-time statistic curve does not repair the peak or the drop related to the specific physical signal. The real-time statistic curve can be rebuild by the stored past statistic curves; moreover, the bio-sensor module continuously receives the physical signals acquired at the following points of time since the specific physical signal is identified, and the real-time statistic curve can be rebuild to form the amended statistic curve by the physical signals acquired before and after the specific physical signal. The rebuild statistic curve displayed on the warning interface is smooth and different from the real-time statistic curve.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
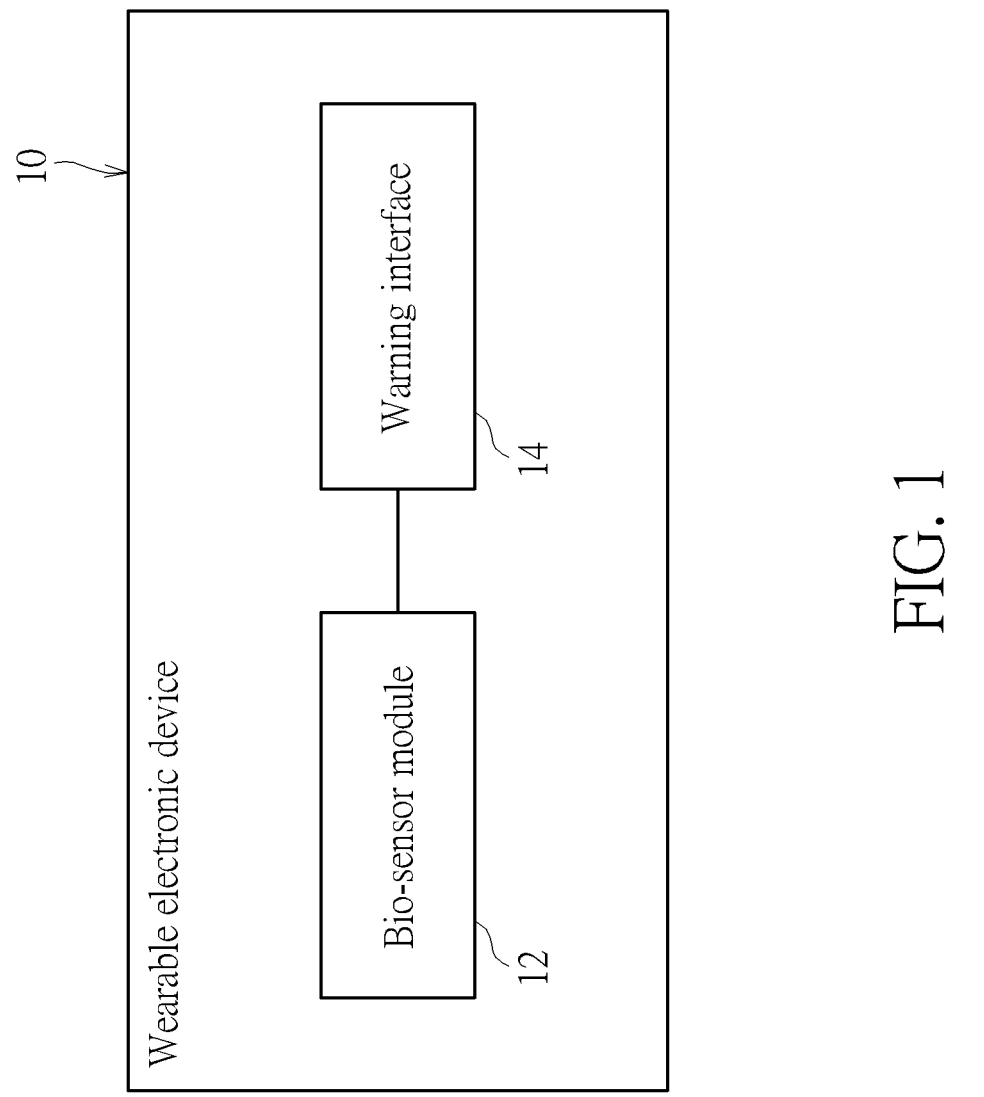
FIG. 1 is a functional block diagram of a wearable electronic device according to an embodiment of the present invention.
Figure 2:
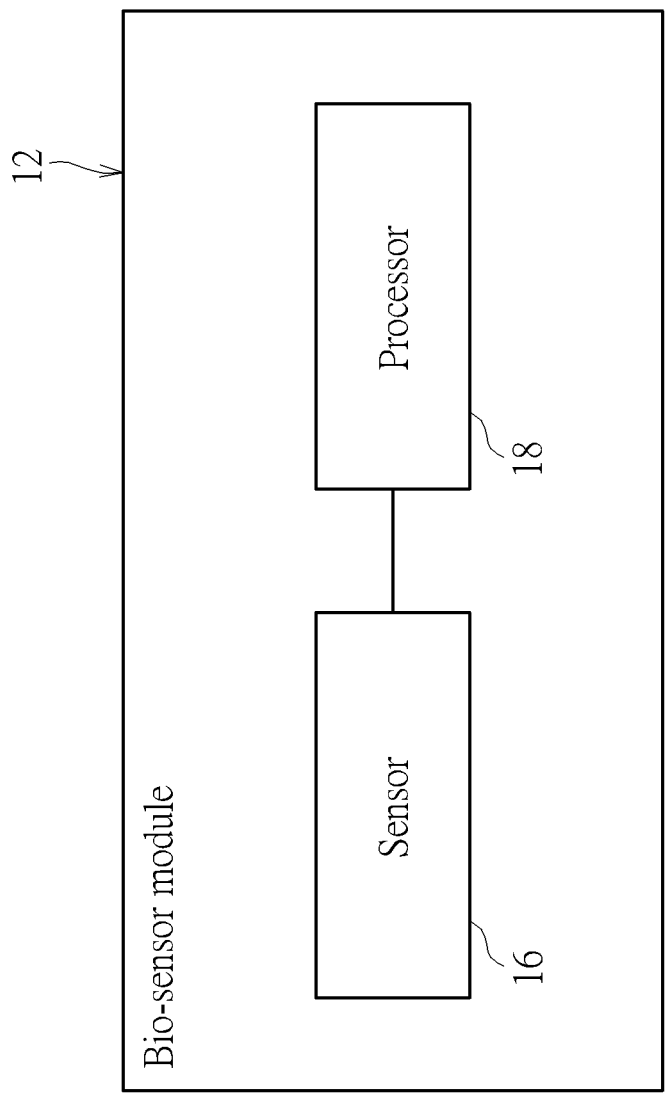
FIG. 2 is a functional block diagram of a bio-sensor module according to the embodiment of the present invention.
Figure 3:
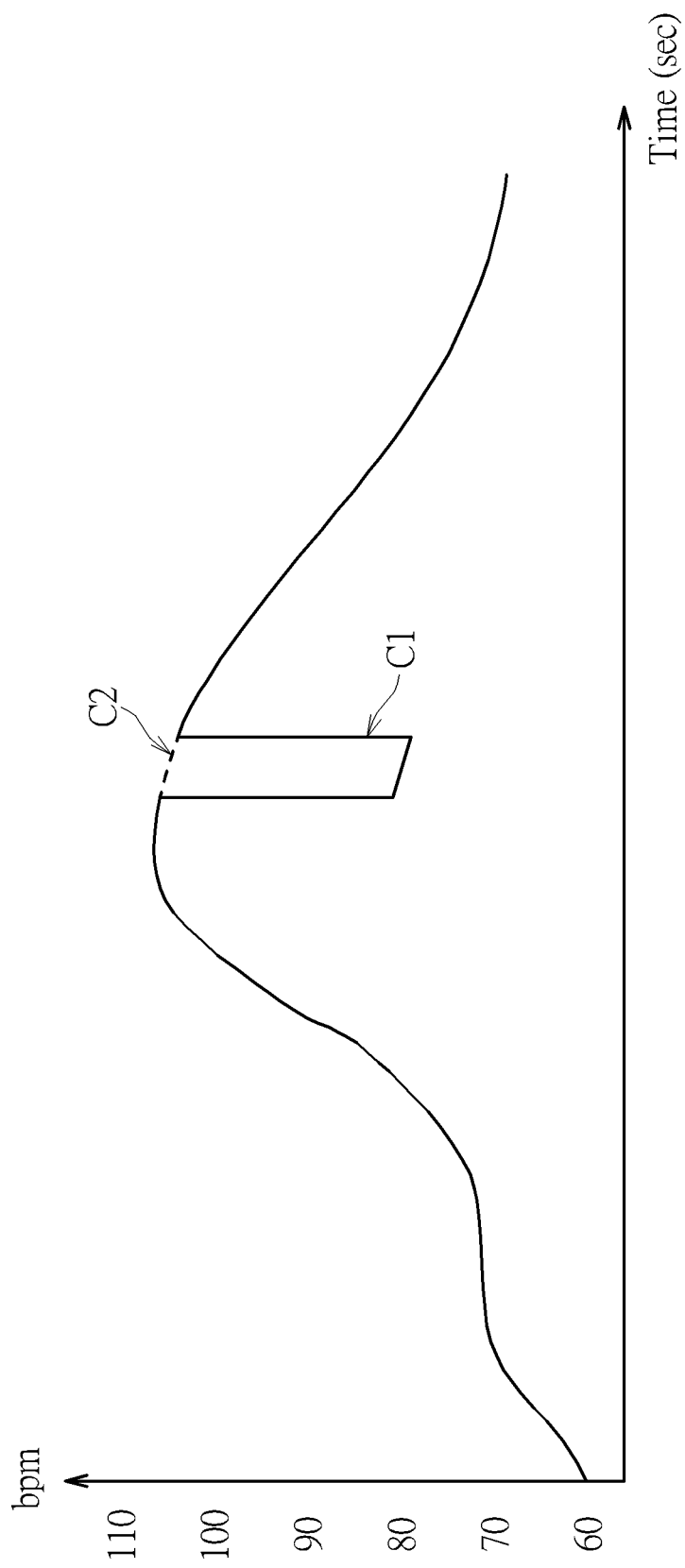
FIG. 3 is a diagram of statistic curves build by the bio-sensor module according to the embodiment of the present invention.

Please refer to FIG. 1 to FIG. 3. FIG. 1 is a functional block diagram of a wearable electronic device 10 according to an embodiment of the present invention. FIG. 2 is a functional block diagram of a bio-sensor module 12 according to the embodiment of the present invention. FIG. 3 is a diagram of statistic curves build by the bio-sensor module 12 according to the embodiment of the present invention. The wearable electronic device 10 can include the bio-sensor module 12 and a warning interface 14, and the bio-sensor module 12 can include a sensor 16 and a processor 18 electrically connected with each other. The sensor 16 senses biometric features of a user, and the processor 18 analyzes and plays the biometric features via the warning interface 14. The warning interface 14 can be a screen utilized to play a visible reminder, or further can be a speaker utilized to play an acoustic reminder.

When the user wears the wearable electronic device 10, the bio-sensor module 12 may close to or touch the user's skin, and the sensor 16 can continuously receive a plurality of physical signals acquired in accordance with sensor data. For example, the sensor data can be information of photoplethysmography, heart rate, or glycermia about the user who wears the wearable electronic device 10. The processor 18 can analyze the physical signals as the statistic curve about a heart rate or a health evaluation (such as blood pressure or blood sugar) within a period of time. The statistic curve can be displayed on the warning interface 14. However, the bio-sensor module 12 may be spaced from the user's skin when the user exercises or interfered by noise when the sensor data is less than a predetermined threshold, so the sensor 16 does not receive correct physical signals at a specific point of time and an accuracy of the statistic curve is affected accordingly. Thus, the processor 18 of the bio-sensor module 12 can filter a specific physical signal acquired at the specific point of time for rebuilding the statistic curve.

In other embodiment, the sensor 16 could be used to detect motion of the user. For example, the sensor data detected by the sensor 16 can be information of acceleration or position of the user who wears the wearable electronic device 10.

Supposing the wearable electronic device 10 is a smart watch, the user can wear the wearable electronic device 10 to sense the heart rate (beat per minute, BPM) when walking, running or swimming. The wearable electronic device 10 is not tightly worn for comfort, which means the bio-sensor module 12 may sometimes leave the skin, and an original detection result of the bio-sensor module 12 shows noise accordingly, as the statistic curve C1 shown in FIG. 3. During some specific points of time, the statistic curve C1 may have an unexpected peak or drop, and the wearable electronic device 10 can output a warning signal for reminder. If the statistic curve C1 is displayed on the warning interface 14 instantaneously, the wearable electronic device 10 can output the warning signal to remind the user that the statistic curve C1 may be affected by the unexpected noise. The wearable electronic device 10 can identify the noise in the statistic curve C1, and further remove and replace the noise by an assuming value, so as to rebuild and display the statistic curve C2 on the warning interface 14, or to transmit the statistic curve C2 toward an external device for other digital operational application.

Figure 6:
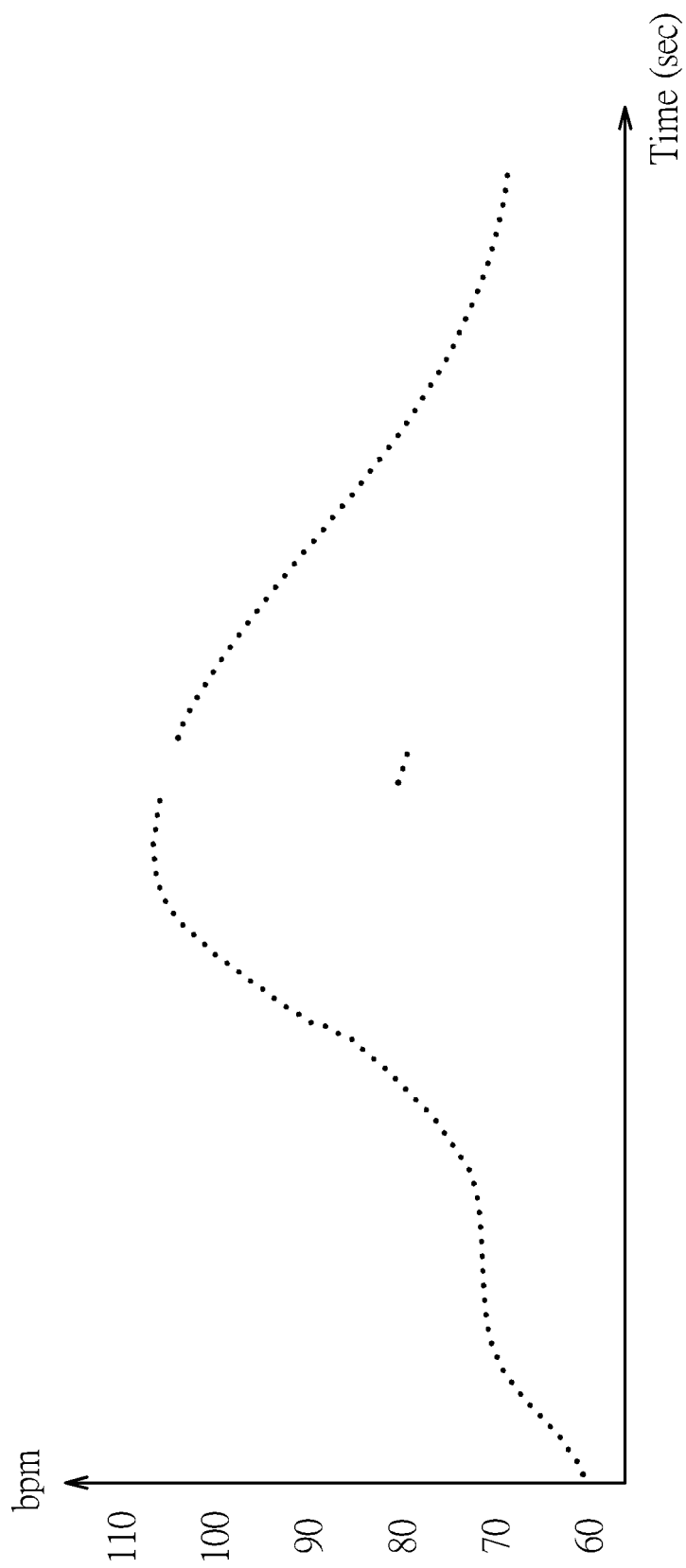
FIG. 6 is a diagram of distribution about the analyzed physical signals according to another embodiment of the present invention.

The analyzed physical signals may be not displayed or formed as the statistic curve. In one embodiment, the analyzed physical signals could be a series of data indicating values corresponding to the statistic curve as showed in FIG. 3. Please refer to FIG. 6. FIG. 6 is a diagram of distribution about the analyzed physical signals according to another embodiment of the present invention. The analyzed physical signals are individually required at each point of time and thereby can be displayed on the warning interface 14 in a discrete manner. One of the physical signals or variation between adjacent physical signals can be used to identify whether the corresponding physical signal meet a predefined condition.

Figure 4:
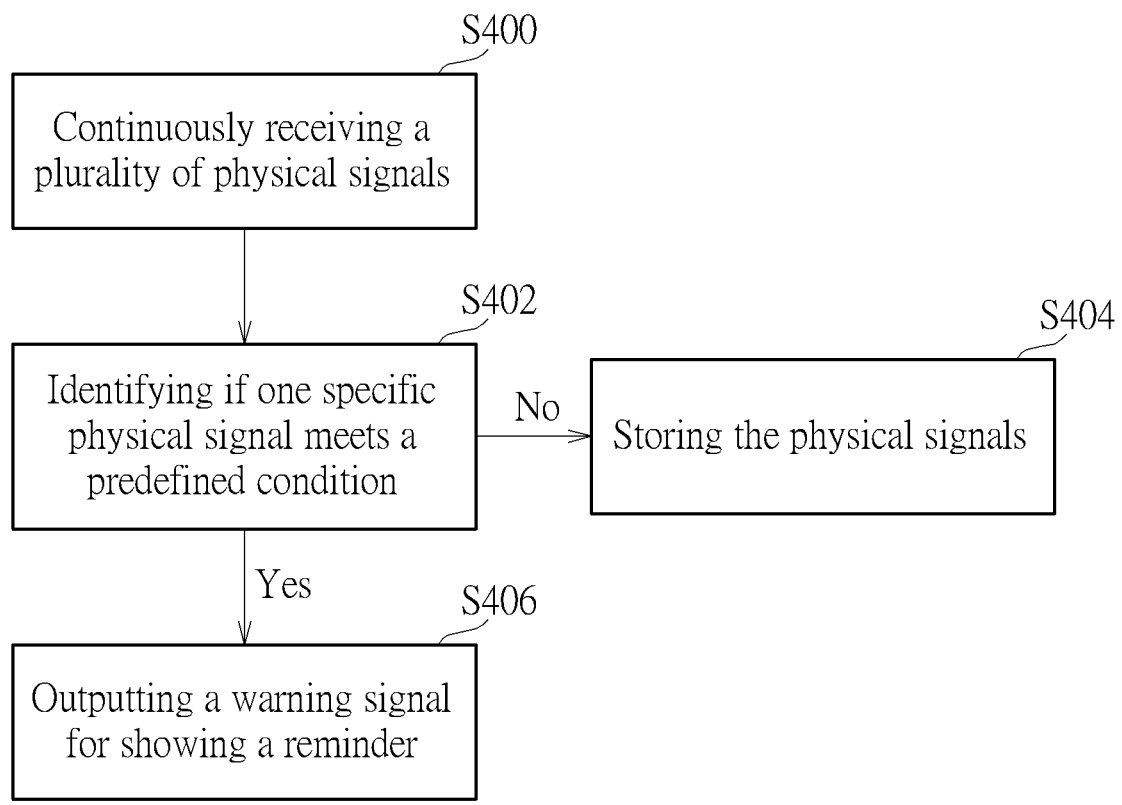
FIG. 4 is a flow chart of a datum warning method applied to the bio-sensor module according to the embodiment of the present invention.

Please refer to FIG. 4. FIG. 4 is a flow chart of a datum warning method applied to the bio-sensor module 12 according to the embodiment of the present invention. First, step S400 is executed that the sensor 16 can continuously receive the plurality of physical signals. The physical signal is not limited to the heart rate as mentioned above, and any parameters capable of indicating the biometric features of the user belong to a scope of the present invention. Then, steps S402 is executed that the processor 18 can identify if one specific physical signal meets the predefined condition. When one of the plurality of physical signals does not meet the predefined condition, step S404 is executed to store the physical signals. When the specific physical signal meets the predefined condition, step S406 is executed to output the warning signal instantaneously for showing the reminder. The user can feel (such as seeing or listening) the reminder to realize that the sensor data from the sensor 16 may be interfered by noise. The bio-sensor module 12 spaced from the user's skin may receive ambient light instead of reflected light from the skin, so the predefined condition can be represented as some of the physical signals having high noise ratio or low intensity.

In step S402, a plurality of specific physical signals may be determined to identify if a predefined condition is met. The datum warning method can set a predefined period, find out the plurality of specific physical signals within the predefined period, and identify whether all the plural specific physical signals or a part of the plural specific physical signals meet the predefined condition. If an amount of the specific physical signals meeting the predefined condition exceeds one threshold, step S406 can be executed accordingly.

It should be mentioned that the predefined condition can be determined by the variation of the plurality of physical signals. For example, when the foresaid variation is greater than a threshold, such as the current physical signal being sharply increased or decreased in a comparison with the previous physical signal, the current physical signal can be represented as meeting the predefined condition. Besides, when the current physical signal is greater than the previous physical signal and the previous physical signal is smaller than the physical signal before the previous physical signal, or the current physical signal is smaller than the previous physical signal and the previous physical signal is greater than the physical signal before the previous physical signal, the current physical signal can be represented as meeting the predefined condition. The datum warning method may also execute the foresaid identification by the variation of the physical signals instead of the single physical signal.

In yet another embodiment, the predefined condition can be correlated to the condition that the specific physical signal is obtained. For example, if a light source driving current exceeds one threshold when obtaining a specific physical signal, then the specific physical signal is determined to meet the predefined condition.

The datum warning method can analyze at least one of an operational parameter and biological evidence generated at each point of time, and identify whether the specific physical signal acquired at the specific point of time meets the predefined condition according to abnormality of the operational parameter or the biological evidence. The operational parameter can be selected from a group consisting of a current, a voltage, an operational frequency, and a combination thereof about the bio-sensor module 12. The biological evidence can be sensed by the bio-sensor 12, and the biological evidence can be the heart rate or any other biological parameter. For instance, when the sensor 16 leaves the user's skin, the operational parameter generated as the specific physical signal is acquired may be inevitably increased or decreased, and the abnormality of inevitably increasing and decreasing can be interpreted as the predefined condition.

In step S406, the datum warning method can output the warning signal right after the specific physical signal is identified, or further can output the warning signal when showing the statistic curve C2 and the reminder on the warning interface 14. The warning interface 14 can not only be a screen adapted to play the visible reminder about the warning signal (such as an exclamation mark) and the statistic curve C1 or C2, but also a speaker adapted to play the acoustic reminder (such as an alarm sound).

Figure 5:
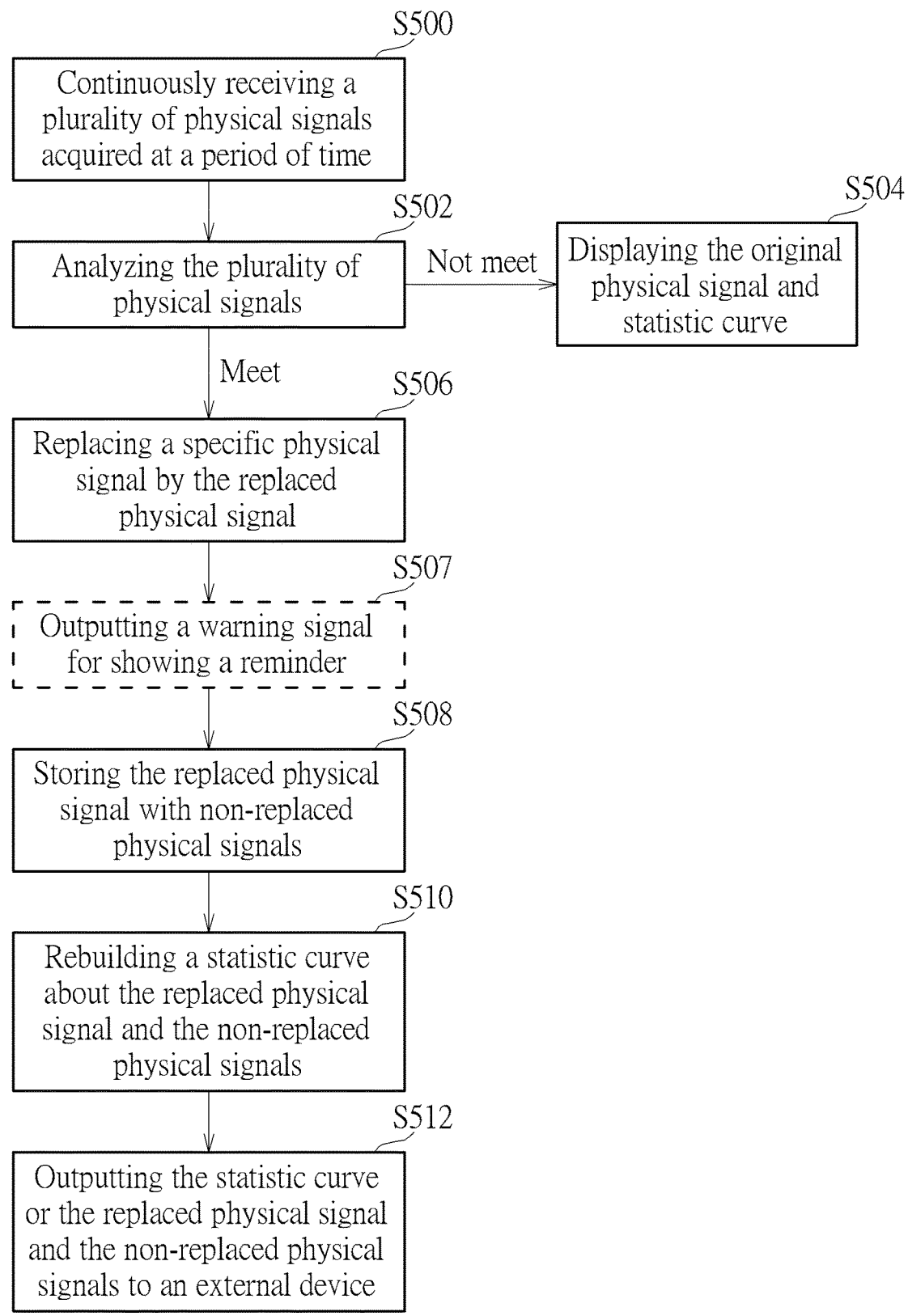
FIG. 5 is a flow chart of a datum rebuilding method applied to the bio-sensor module according to the embodiment of the present invention.

Please refer to FIG. 5. FIG. 5 is a flow chart of a datum rebuilding method applied to the bio-sensor module 12 according to the embodiment of the present invention. First, step S500 is executed that the bio-sensor 12 can continuously receive the plurality of physical signals acquired at the period of time. Then, step S502 is executed that the processor 18 can analyze and display the plurality of physical signals. Analysis of the physical signal can be identifying if any specific physical signal meets the predefined condition. When the physical signal does not meet the predefined condition, step S504 is executed to display the original physical signal and the original statistic curve. When the physical signal is specific and meets the predefine condition, steps S506 and S508 are executed to replace the specific physical signal by the replaced physical signal, and then store the replaced physical signal with non-replaced physical signals into a memory of the wearable electronic device 10. Final, steps S510 and S512 are executed that the processor 18 can rebuild the statistic curve C2 about the replaced physical signal and the non-replaced physical signals, and further output the statistic curve C2 to the external device (such as the warning interface 14) for showing the visible result or output the replaced physical signal and the non-replaced physical signals to another host for the digital operational application.

When the specific physical signal is identified as meeting the predefine condition, step S507 can be optionally executed to output the warning signal for showing at least one of the visible reminder and the acoustic reminder. The foresaid warning signal can be output right after the specific physical signal is identified or when the statistic curve is rebuild. In step S502, each of the physical signals can be compared with the adjacent physical signals acquired at the previous point and the following point of time. Any physical signal having the unusual high noise ratio or the unusual low intensity (which is compared with the noise and the intensity of the previous and following physical signals) can be determined as being specific and abnormal, and the specific physical signal acquired at the specific point of time can be filtered and replaced accordingly for rebuilding the smooth statistic curve.

As mentioned above, the replaced physical signal can be computed not only by the adjacent physical signals, but also by the similar physical signals of the past statistic curve stored in a database of the wearable electronic device 10. For example, the replaced physical signal can be a maximum, a minimum or an average of the adjacent physical signals acquired at the previous point and the following point of time. In addition, the database may optionally store several past statistic curves build by the bio-sensor 12, and the physical signals of the past statistic curves are known; therefore, the replaced physical signal can be a maximum, a minimum, an average, or any of the known physical signals acquired at similar points of time, so the peak and/or the drop of the statistic curve C1 can be repaired to rebuild the statistic curve C2 for preferred user experience.

In the present invention, the bio-sensor module 12 can receive the physical signals when the wearable electronic device 10 is actuated and worn by the user. As the bio-sensor module 12 leaves the user's skin, the specific physical signal is identified and the wearable electronic device 10 can output the reminder via the warning interface immediately, but the real-time statistic curve C1 does not repair the peak or the drop related to the specific physical signal. The real-time statistic curve C1 can be rebuild by the stored past statistic curves; moreover, the bio-sensor module 12 continuously receives the physical signals acquired at the following points of time since the specific physical signal is identified, and the real-time statistic curve C1 can be rebuild to form the amended statistic curve C2 by the physical signals acquired before and after the specific physical signal. The rebuild statistic curve C2 displayed on the warning interface is smooth and different from the real-time statistic curve C1.

Comparing to the prior art, the wearable electronic device of the present invention can filter the unexpected peak or drop of the original sensing results and instantaneously output the warning signal for the visible, acoustic or tactile reminder, and then repair the unexpected peak or drop to rebuild the smooth statistic curve displayed on the screen for showing the reliable user's experience.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A datum rebuilding method applied to a bio-sensor module equipped in a wearable electronic device, comprising:
    continuously receiving a plurality of physical signals acquired within a period of time;
    displaying each of the physical signals; and
    replacing at least one of the physical signals and then storing the replaced physical signal with non-replaced physical signals before outputting to an external device;
    wherein the replaced physical signal is sourced from a database, the database is configured to store at least one past statistic curve build by the bio-sensor module, and the replaced physical signal is computed by the physical signals of the at least one past statistic curve acquired at similar points of time.

2. A wearable electronic device with a datum rebuilding function and a datum warning function, comprising:

a warning interface; and a sensor module coupled with the warning interface, the sensor module comprising:

a sensor adapted to continuously receive a plurality of physical signals acquired within a period of time; and a processor electrically connected with the sensor, the processor being adapted to display each of the physical signals via the warning interface, and replace at least one of the physical signals and then store the replaced physical signal with non-replaced physical signals for rebuilding a statistic curve;

wherein the replaced physical signal is sourced from a database, the database is configured to store at least one past statistic curve build by the bio-sensor module, and the replaced physical signal is computed by the physical signals of the at least one past statistic curve acquired at similar points of time.

3. The wearable electronic device of claim 2, wherein the processor is adapted to rebuild the statistic curve by the replaced physical signal and the non-replaced physical signals for showing a visible result on the external device.

4. The wearable electronic device of claim 2, wherein the warning interface is a screen adapted to play a visible reminder about the warning signal and the statistic curve, or a speaker adapted to play an acoustic reminder about the warning signal.

* * * * *